United States Patent [19]
Ishikawa

[11] Patent Number: 5,825,036
[45] Date of Patent: Oct. 20, 1998

[54] ELECTROMAGNETIC WAVE RADIATION METHOD AND DEVICE

[76] Inventor: Eizo Ishikawa, 311-24,6 Chome Hinode, Itaco-cho Ibaragi Prefecture, Japan

[21] Appl. No.: 671,334

[22] Filed: Jun. 27, 1996

[30] Foreign Application Priority Data

Jan. 29, 1996 [JP] Japan ................................ 8-045276

[51] Int. Cl.⁶ ........................................... H01J 37/00
[52] U.S. Cl. ................................ 250/492.1; 250/455.11
[58] Field of Search ................. 250/492.1, 455.11; 422/22

[56] References Cited

U.S. PATENT DOCUMENTS 5,087,418  2/1992  Jacob ........................... 250/492.1
5,247,179  9/1993  Tachibana ..................... 250/492.1

*Primary Examiner*—Kiet T. Nguyen
*Attorney, Agent, or Firm*—Blank Rome Comisky & McCauley LLP

[57] ABSTRACT

A weak electromagnetic wave radiation method and device are employed to generate weak electromagnetic waves and to radiate a subject with the weak electromagnetic waves, thereby enabling essential function recovery or activation in the subject being radiated. A weak magnetic field is generated, and is passed through an ultra-small weak electromagnetic wave radiating material to produce the weak electromagnetic waves, and the subject is then radiated with the weak electromagnetic waves. Subjects which benefit from the disclosed method and device include human tissue, plants, vegetables, foodstuffs, water and textile products.

17 Claims, 1 Drawing Sheet

ELECTROMAGNETIC WAVE RADIATION METHOD AND DEVICE

TECHNICAL FIELD

The present invention generally relates to a weak electromagnetic wave radiation method and device that can radiate weak electromagnetic waves and enable essential function recovery or activation in a subject.

BACKGROUND ART

Radiation of electromagnetic waves can be used on all living tissue as a means for promoting rehabilitation of tissue, including human tissue, and for strengthening and revitalizing all sorts of essential tissue, such as activating various components of plants and vegetables and water related to life.

Hitherto, the radiating materials with wavelengths shorter than 10 μm which have been used are ceramic and synthetic composite materials or electro-optical sources, such as infrared lamps or UV lamps or x-ray devices, so that fine control of energy has been very difficult. For example, it has been impossible to electrically output $4 \times 10^{-3}$ watt.

DISCLOSURE OF INVENTION

The present invention generally relates to a weak electromagnetic wave radiation method and device that can radiate weak electromagnetic waves and enable essential function recovery or activation in a subject.

A primary object of the present invention is to use weak magnetism to generate weak electromagnetic waves so as to irradiate a target with effective radiation without using the previously described electro-optical sources or x-ray generating devices of the prior art. In accordance with the present invention, a weak output with wavelength shorter than 10 μm and energy level of about $4 \times 10^{-3}$ watt can be transmitted with a weak magnetic field (50 to $5,000 \times 10^{-5}$ gauss).

Thus, using an ultra-small weak electromagnetic wave radiating material of 10 to $1 \times 10^{-6}$ μm, weak magnetism of 50 to $5,000 \times 10^{-5}$ gauss is caused to pass through a subject. When weak magnetism is caused to pass through an ultra-small weak electromagnetic wave radiating material, weak electromagnetic waves irradiate the subject in proper quantity.

Therefore, it is a primary object of the present invention to provide a weak electromagnetic wave radiation method and device.

It is an additional object of the present invention to provide a weak electromagnetic wave radiation method and device that can radiate weak electromagnetic waves.

It is an additional object of the present invention to provide a weak electromagnetic wave radiation method and device that can enable essential function recovery or activation in a subject.

The above and other objects, and the nature of the invention, will be more clearly understood by reference to the following detailed description, the associated drawings, and the appended claims.

BEST MODE FOR CARRYING OUT THE INVENTION

The invention will now be described in more detail with reference to the various figures of the drawings.

Figure 1:
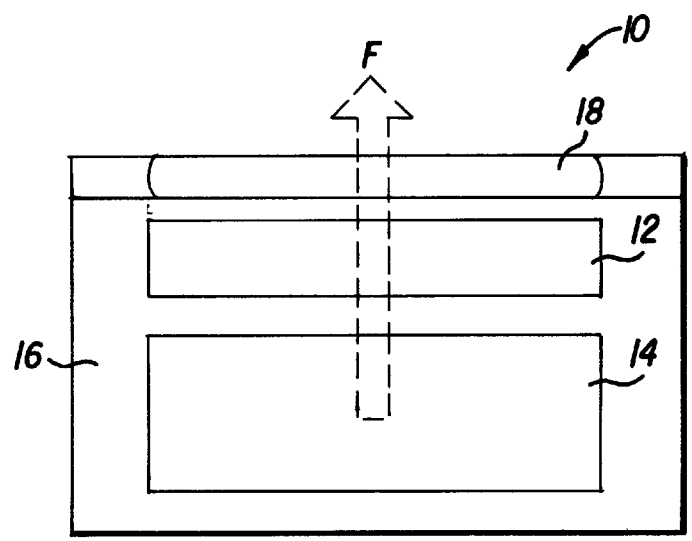
FIG. 1 is a diagrammatic representation of the basic structure of the device of the present invention.

FIG. 1 is a diagrammatic representation of the basic structure of the device of the present invention. As seen therein, the device 10 of the present invention generally comprises ultra-small weak electromagnetic wave radiating material 12, magnetism-generating structure 14, housing 16, and heater 18.

In operation, weak magnetism generated by structure 14 passes through electromagnetic wave radiating material 12, and is radiated at the subject (not shown) in the direction of the arrow F. In this case, weak magnetism of 50 to $5,000 \times 10^{-5}$ gauss is caused to pass through the weak electromagnetic wave radiating material 12 (wavelength 10 to $1 \times 10^{-6}$ μm), composed of a laminated composite material, and the resultant weak electromagnetic waves are appropriately radiated at the subject in the direction of the arrow F. In the latter embodiment, heater 18 is not an essential component, but can be provided if necessary or desired.

Figure 2:
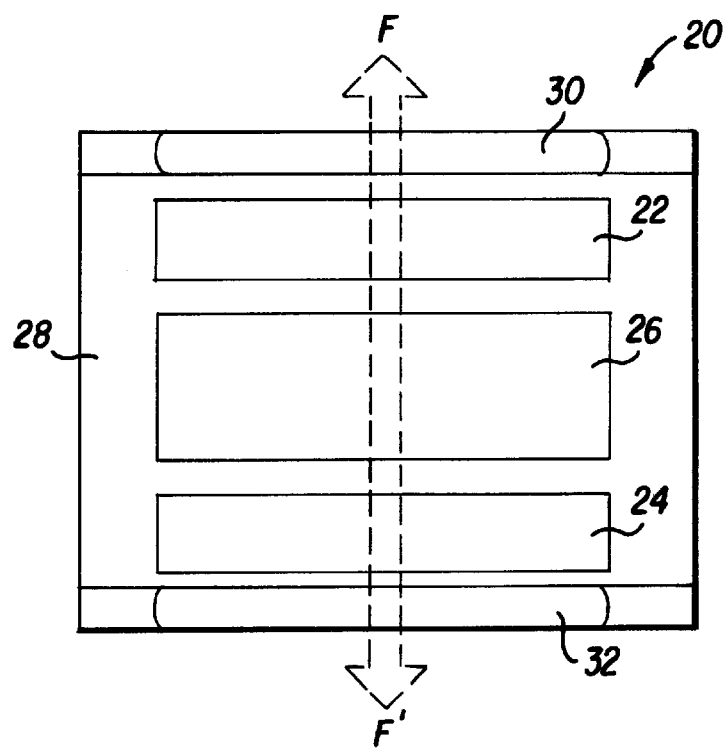
FIG. 2 is a diagrammatic representation of a further embodiment of the invention.

FIG. 2 is a diagrammatic representation of a further embodiment of the invention. As seen therein, the device 20 of FIG. 2 comprises electromagnetic wave radiating materials 22 and 24, magnetism-generating structure 26, housing 28, and heater 30.

The device 20 of FIG. 2 achieves the same results as the device 10 of FIG. 1. Thus, weak magnetism generated by structure 26 passes through weak electromagnetic wave radiating materials 22 and 24, the materials 22 and 24 being arranged in parallel on respective sides of the structure 26. The weak magnetism is radiated at the subject (not shown) in the directions indicated by the two-headed arrow F'. As was the case in FIG. 1, weak magnetism of 50 to $5,000 \times 10^{-5}$ gauss is caused to pass through the weak electromagnetic wave radiating materials 22 and 24, and the resultant weak electromagnetic waves are appropriately radiated at the subject in the directions indicated by the double-headed arrow F'. In this embodiment, as was the case in the previously described embodiment, the heater 32 is not an essential component, but can be utilized if needed or desired.

In accordance with the basic concept and device of the present invention, dramatic function and effect can be achieved in objects, even with simple structure, and thus the categories indicated in the following tables were adopted because of the ease with which experimentation can be conducted and evaluation values calculated. The following examples show the results of experimentation in which the concept and device of the present invention were employed with respect to biological tissue recovery power, plant and vegetable activation, foodstuff functioning, water activation and functioning, and clothing functioning.

BIOLOGICAL TISSUE RECOVERY POWER

| SUBJECT HUMAN | SEX | AGE | BEFORE PROOF | AFTER PROOF |
|---|---|---|---|---|
| A | M | 49 | Walking difficult due to hernia | In 1 minute walked and bent and stretched |
| B | M | 54 | 20 years of chronic back pain | Alleviated in 5 minutes |
| C | M | 52 | Chronic irregular pulse | Became regular after 2 minutes |
| D | F | 53 | Right shoulder [illeg.] 1 year | Lifted 45–120° after 40 minutes |
| E | M | 55 | Trembling hand | Stopped trembling in 1 minute |
| F | M | 60 | Chronic back pain; right | Alleviated in 30 minutes |

| SUBJECT HUMAN | SEX | AGE | BEFORE PROOF | AFTER PROOF |
|---|---|---|---|---|
| G | F | 47 | leg numb Chronic [illeg.] in neck and shoulder | Alleviated in 30 minutes |

Conclusion: Dramatic effects were observed.

PLANT AND VEGETABLE ACTIVATION

| TEST MATERIAL | EXPERIMENT METHOD | CONCLUSION |
|---|---|---|
| 6 shriveled oranges | Apply tap water to test item. Wrap each of six individually. 5 minutes in device; then let sit 3 hours. | Returned to vivid color |
| 6 shriveled oranges | Apply tap water to test item. Wrap each of six individually; then let sit 3 hours. | Shriveled state unchanged |

FOODSTUFF FUNCTIONING

Experimental Method

Put 5 kg salt on device for 1 minute. Measure before and after with magnetic resonance device (BICS). In the table, "Code No." indicates the BICS number, and the values at the right range from −21 to 0 to +21, with +21 indicating maximum and −21 indicating minimum value.

| ITEM INSPECTED | | | |
|---|---|---|---|
| ITEM | CODE NO. | SAMPLE BEFORE | SAMPLE AFTER |
| Immune function | 2BD6 | +9 | +21 |
| Pituitary gland | 3411 | +10 | +21 |
| Hormone balance | 325F | +5 | +21 |
| Allergy | 3FFF | +9 | +21 |
| Heart | 336E | +5 | +21 |
| Stomach | 338F | +3 | +21 |
| Liver | 33D9 | +7 | +21 |
| Autonomic nerves | 30F8 | +4 | +21 |
| Diabetes | 35DD | +7 | +21 |
| High blood pressure | 34D0 | +5 | +21 |
| Kidney | 35EA | +7 | +21 |
| Kidney tissue | 36C0 | +7 | +21 |
| Heart muscle | 3349 | +9 | +21 |
| Hardening of the arteries | 3B8C | +7 | +21 |
| Cardiac insufficiency | 4A3D | +4 | +21 |
| Cancer | 3A9D | +7 | +21 |

Conclusion: Salt's functioning was dramatic.

WATER ACTIVATION AND FUNCTIONING

Leave two liters of tap water in the device for one minute and measure with magnetic resonance device (BICS).

| ITEM INSPECTED | | | |
|---|---|---|---|
| ITEM | CODE NO. | SAMPLE BEFORE | SAMPLE AFTER |
| Immune function | 2BD6 | +4 | +21 |
| Pituitary gland | 3411 | +3 | +21 |
| Hormone balance | 325F | +4 | +21 |
| Allergy | 3FFF | +2 | +21 |
| Heart | 336E | +4 | +21 |
| Stomach | 338F | +2 | +21 |
| Liver | 33D9 | +4 | +21 |
| Autonomic nerves | 30F8 | +3 | +21 |
| Diabetes | 35DD | +4 | +21 |
| High blood pressure | 34D0 | +3 | +21 |
| Kidney | 35EA | +4 | +21 |
| Kidney tissue | 36C0 | +3 | +21 |
| Heart muscle | 3349 | +4 | +21 |
| Hardening of the arteries | 3B8C | +3 | +21 |
| Cardiac insufficiency | 4A3D | +4 | +21 |
| Cancer | 3A9D | +3 | +21 |

Conclusion: Water's functioning was high.

CLOTHING FUNCTIONING

| TEST MATERIAL | Six 100% silk scarves (same color) |
|---|---|
| TEST METHOD | Three scarves left in the device for five minutes and three untreated scarves were mixed together and given to two men and two women who then selected the scarves with superior warmth. |
| RESULTS | The two men and two women decided the scarves put in the device were better (warmth as selection reason). |

To summarize, the invention is based on the principle that the passing of weak magnetism thru an ultra-small weak electromagnetic wave radiation material generates weak electromagnetic waves which can be used to radiate a subject. According to the invention, the weak electromagnetic wave radiation material is placed on a structure which generates weak magnetism, and as a result ultra-small weak electromagnetic waves are generated and can be used to radiate the subject. Reactivation or activation of tissue in a radiated subject can be expected as a result of implementation of the invention. When the subject is a human being, the recovery power of an organ is increased. When the subject is a plant or vegetable, its tissue, activation and growth are promoted. Additionally, the present invention has wide application for the structure of objects used in daily life, such as textile products.

Thus, the invention is utilized to implement a simple and safe weak electromagnetic wave radiation device which radiates appropriate quantities of weak electromagnetic waves at the previously described subjects, thereby enabling essential function recovery or activation in the targeted areas and improvement of properties. A device structured according to the basic principle of the present invention modifies the magnetic coil current value of the device, and thereby usefully changes the efficiency of radiating weak electromagnetic waves at a subject.

While preferred forms and arrangements have been shown in illustrating the invention, it is to be understood that various changes and modifications may be made without departing from the spirit and scope of this disclosure.

I claim:

1. A weak electromagnetic wave radiating method, comprising the steps of:

applying a weak magnetic field having a $50 \times 10^{-5}$ to $5,000 \times 10^{-3}$ gauss to a weak electromagnetic wave radiating material, to radiate a weak electromagnetic wave having a wavelength of 10 to $1\times10^{-6}$ μm; and applying the radiated weak electromagnetic wave to a subject, to activate energy of the subject.

2. The method of claim 1, wherein said subject comprises human tissue.

3. The method of claim 1, wherein said subject comprises one of plants and vegetables.

4. The method of claim 1, wherein said subject comprises foodstuffs.

5. The method of claim 1, wherein said subject comprises water.

6. The method of claim 1, wherein said subject comprises textile products.

7. The method of claim 1, further comprising the step of heating the weak electromagnetic wave prior to applying said radiated weak electromagnetic wave to said subject.

8. A weak electromagnetic wave radiating apparatus, comprising:

a weak magnetic field generating apparatus for generating a weak magnetic field having $50\times10^{-5}$ to $5,000\times10^{-31}$ gauss; and a weak electromagnetic wave radiating material for radiating a weak electromagnetic wave having a wavelength of 10 to $1\times10^{-6}$ μm, by application of said weak magnetic field generated in said weak magnetic field generating apparatus, wherein said weak electromagnetic wave radiated from said weak electromagnetic wave radiating material is applied to a subject, to activate energy of said subject.

9. The apparatus of claim 8, wherein said weak electromagnetic wave radiating material comprises a laminated composite material.

10. The apparatus of claim 8, wherein said weak electromagnetic wave radiating material has a wavelength substantially in the range of 10 to $1\times10^{-6}$ μm.

11. The apparatus of claim 8, wherein said generating apparatus generates a weak magnetic field having a strength substantially in the range of 50 to $5,000\times10^{-5}$ gauss.

12. The apparatus of claim 8, wherein said subject comprises human tissue.

13. The apparatus of claim 8, wherein said subject comprises one of plants and vegetables.

14. The apparatus of claim 8, wherein said subject comprises foodstuffs.

15. The apparatus of claim 8, wherein said subject comprises water.

16. The apparatus of claim 8, wherein said subject comprises textile products.

17. The apparatus of claim 8, further comprising heating means for heating said weak electromagnetic wave prior to applying said radiated weak electromagnetic wave to said subject.

* * * * *